(12) United States Patent
Kohl et al.

(10) Patent No.: US 6,461,414 B1
(45) Date of Patent: Oct. 8, 2002

(54) FOAM MONITORING AND CONTROL SYSTEM

(75) Inventors: Kristopher T. Kohl, Houston; Christopher Gallagher, Katy; C. Mitch Means, Richmond, all of TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/699,018

(22) Filed: Oct. 27, 2000

Related U.S. Application Data

(60) Provisional application No. 60/162,542, filed on Oct. 29, 1999.

(51) Int. Cl.⁷ .............................................. B01D 19/02
(52) U.S. Cl. ................................ 96/156; 95/1; 95/242; 96/176
(58) Field of Search ............................ 95/1, 155, 241, 95/242; 96/156, 176, 181

(56) References Cited

U.S. PATENT DOCUMENTS

| | | | |
|---|---|---|---|
| 1,921,725 A | * | 8/1933 | Boutet |
| 3,739,795 A | * | 6/1973 | Hyde et al. |
| 4,018,089 A | | 4/1977 | Dzula et al. ............... 73/422 R |
| 4,426,879 A | | 1/1984 | Humphries et al. ........... 73/60.1 |
| 4,444,044 A | | 4/1984 | Humphries et al. ........... 73/60.1 |
| 4,596,586 A | | 6/1986 | Davies et al. .................... 55/52 |
| 4,624,745 A | * | 11/1986 | Sande et al. |
| 5,437,842 A | * | 8/1995 | Jensen et al. |
| 5,547,022 A | | 8/1996 | Juprasert et al. ............. 166/263 |
| 5,593,890 A | * | 1/1997 | Flores-Coterea et al. |
| 5,853,617 A | | 12/1998 | Gallagher et al. ........... 252/321 |
| 5,868,859 A | | 2/1999 | Hei et al. ....................... 134/18 |
| 5,922,112 A | * | 7/1999 | Zappi et al. |

FOREIGN PATENT DOCUMENTS

EP 0 859 235 A1 8/1998

* cited by examiner

Primary Examiner—Duane S. Smith
(74) Attorney, Agent, or Firm—Madan, Mossman & Sriram, P.C.

(57) ABSTRACT

A system for monitoring foaming or carry over, at a well site, of a formation fluid by taking a sample of the gas exiting from a high-pressure separator and either measuring the density of the sample or measuring the amount of oil particles present. A correlation of the density or optical density with a level of foaming is made and a signal is transmitted to a device to control the supply of at least one additive to control the foaming.

17 Claims, 2 Drawing Sheets

FOAM MONITORING AND CONTROL SYSTEM

CROSS-REFERENCE TO RELATED APPLICATIONS

This application takes priority from U.S. patent application Ser. No. 60/162,542 filed Oct. 29, 1999.

BACKGROUND OF THE INVENTION

1. Field of the Invention

This invention relates generally to oil producing operations, and more particularly to a system and a method for monitoring and controlling foam or hydrocarbon carry over at a wellsite.

2. Background of the Invention

Oil, also referred to herein interchangeably as crude oil, condensate, or formation fluid, in essentially all reservoirs contains at least some dissolved gases, which exist naturally in the formation. When oil flows upward from the formation through the wellbore(s) to the wellhead, there is a substantial decrease in the pressure because the platform equipment is set up to reduce the high reservoir pressure to a pressure that can be handled by a pipeline system or other downstream equipment. As a result of this drop in system pressure, some of the dissolved gases tend to evolve and become physically separated from the oil to form gas bubbles, i.e. foams.

Although the amount of gases originally dissolved in the oil may not be very large, the effect of lower pressure on their separation can be quite substantial. This is because the same weight of a gas occupies a much larger volume than the corresponding liquid. Depending on the molecular weight, temperature and other conditions, it is not unusual for a small amount of liquid to transform into gas with 100 times or even higher volume. Examples of commonly encountered and naturally occurring gases in formation fluid include, but are not limited to, methane, ethane, carbon dioxide and mixtures.

There is typically a train of several liquid and gas separators installed at a wellsite to separate gases from the oil (liquid) before the oil is processed or transported. In an ideal situation, the evolved gases and oil should separate relatively fast because they are in separate phases and the gas phase bubbles should break out of the fluid phase readily. For a number of reasons, however, the oil-gas separation in practice is usually difficult and incomplete. The main reason is that the gas bubbles in the oil (also referred to as emulsions or foams) are too stable to be effectively broken up at a high oil production rate even with several gas-oil separators because the residence time of the liquid in each separator is kept relatively short. In view of the fact that the industry trend is to have even higher production rate from a producing well, i.e even shorter residence times in the separators, and drilling into formations in deeper water, the problem with foaming may become even more severe. While it is certainly possible to build and use larger gas-oil separators, this option may not be desirable or practical because such separators would require much higher capital investments and more space on oilfield platforms.

Foaming is undesirable because it is usually an unpredictable and metastable phenomenon, which may interfere with the gas-oil separation efficiency or the operations of the oil well(s); the resultant carryover of liquid in the form of either foam or mist/droplets of oil entrained in the gas stream exiting the gas-oil separators will enter into downstream equipment or pipeline. Too much of such liquid carryover can cause severe operating problems, such as flooding for the downstream gas transportation equipment, pipeline or gas processing plants.

One reason for the existence of stable foam, thus the foaming problem, is that many surfactants exist naturally in or near the producing formations. Such surfactants, with their ability to stabilize emulsions or foams, cause the foaming problem to become more pronounced and longer lasting, particularly when the formation fluid reaches the production facilities at the wellhead on the surface as noted above. Moreover, many chemicals or additives are injected into oil wells by the operator to provide functions such as corrosion inhibition, asphaltenes suppression, etc. and may also act as surfactants under the producing conditions to further stabilize the emulsions, thus exacerbating the foaming problem.

Another factor affecting foaming occurs when the formation fluid flows from the producing formation toward the wellbores of the producing wells. The flow rate near the wellbores becomes higher than that in other parts of the reservoir. This higher flow rate tends to cause the formation fluid to trap and mix with any water that may be in the vicinity of the wellbore, or any steam that is injected into the wellbore by the operator. In the presence of either natural or injected chemicals behaving as a surfactant, this type of oil-water emulsion also can further intensify the foaming problem at or down stream from the wellhead.

In typical land or offshore oil production wells, the formation fluid from the wellbores flows through a wellhead choke into a high pressure manifold, which is used if there are multiple wells at a particular site. The fluid then passes through one or more heat exchangers to recover useable heat into a high-pressure (HP) gas-oil separator. There are usually several separators—a train of separators—for one oil processing platform. The primary functions of these separators are to separate the gas and liquid components of the oil and to reduce the pressure in a stepwise manner. Such a train of separators commonly comprises a HP separator, an intermediate pressure (IP) separator, a low-pressure (LP) separator, and a test separator, with the HP separator being closest to the wellhead choke and having the largest pressure drop. In order to conserve energy by not having to repressurize, it is preferred to separate gas from oil at as high a pressure as possible.

The gas phase of the production fluid rapidly expands downstream of the wellhead choke, and continues to expand further downstream through pressure control valves as the fluid travels through the train of gas-oil separators. Any natural surfactants or other additives injected into the well which can act as surfactants tend to create a foaming problem more often in separator vessels with rapid pressure drops, such as the HP separator which have the greatest pressure drop, than the remaining separators in the train of separation.

It is therefore desirable to have a reliable system to determine the extent of foaming of the formation fluid recovered through a wellbore at the wellsite. It is also desirable to use the obtained foaming information to control foaming at the wellsite. The present invention addresses the above-noted needs and provides a wellsite foam monitoring and controlling system which (a) determines the extent of foaming, (b) determines the extent of the treatment required to alleviate the foaming problem, and (c) controls the dispensing of additives to inhibit or alleviate the foaming problem.

SUMMARY OF THE INVENTION

The present invention provides a system for determining and controlling foaming, particularly at a wellsite, of a formation fluid passing through at least one liquid and gas separator that provides a gas stream separated from the formation fluid. The system comprises a sensor, such as a densitometer or a transmission probe, for providing measurements of a parameter of interest relating to the gas stream that are indicative of foaming of the formation fluid, and a processor utilizing the sensor measurements for determining degree of foaming of the formation fluid.

The present invention also relates the aforementioned system which further comprises a gas separation device, such as a quill, for separating a portion of gas, a side stream, from the gas stream and the sensor provides the measurements utilizing the side stream. In another embodiment of the present invention, the sensor is a particle-detecting sensor based on light scatter or transmission configured in the above described sidestream technique or by insertion of a transmission probe directly into the vessel or pipeline.

In another aspect of the invention, there is a chemical injection unit for supplying a chemical to the formation fluid for optionally controlling foam of the formation fluid. The chemical injection unit injects the chemical at one or more of the following location; (i) in one or more of the liquid gas separators; (ii) in a well producing the formation fluid; (iii) a wellhead at the surface; (iv) a selected number of wells from a plurality of wells providing formation fluid to the separator(s). The chemical injection is increased when the degree of foaming is outside a predefined limit.

BRIEF DESCRIPTION OF THE DRAWINGS

For a detailed understanding of the present invention, reference should be made to the following detailed description of the preferred embodiments, taken in conjunction with the accompanying drawings, in which like elements have been given like numerals, wherein.

DETAILED DESCRIPTION OF THE PREFERRED EMBODIMENTS

This invention relates to a system and method for monitoring and controlling foaming at the wellsite. The monitoring is carried out by either monitoring a gas stream directly or by first taking a slipstream (also referred to interchangeably herein as a sidestream) sample from the gas stream exiting a separator and then determining the amount of carried-over liquid in the sidestream. A density measurement of the sidestream is preferred. The measured sidestream density is correlated with the amount of extent or liquid in the sidestream. This amount is a function of and proportional to the degree of foaming in the particular separator or other equipment. The system may further include a chemical injection unit which alters the amount of chemicals injected into the formation fluid to reduce or eliminate foaming of the formation fluid.

Figure 1:
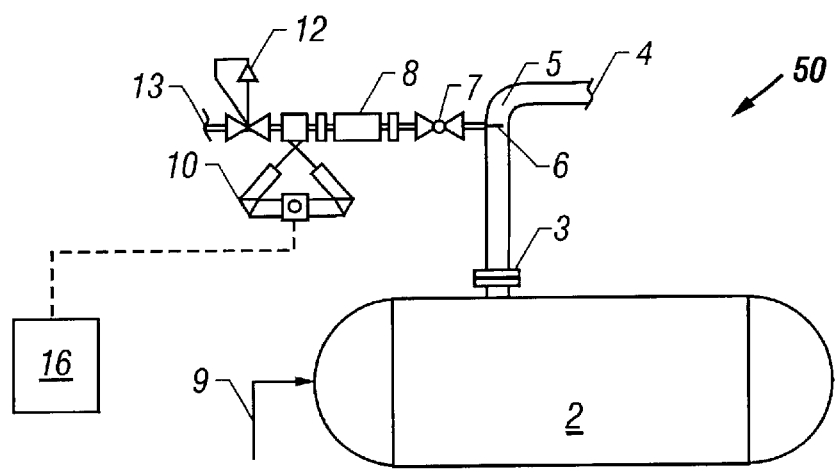
FIG. 1 illustrates a foam or carry over monitoring system according to one embodiment of the present, wherein a densitometer is used to measure the density of a gas stream exiting an HP oil-gas separator.

Illustrations of examples of the preferred systems and methods of the present invention are provided below. FIG. 1 shows a portion of a foam monitoring system in accordance with one embodiment of the present invention. The system includes a high-pressure liquid gas separator 2 which receives formation fluid from the wellhead via line 9. The separator 2 separates oil, water and any other liquids from vaporous gas 5, which gas exits via a pipe 3 to a gas outlet 4 which is connected to other separators such as an IP separator (not shown). A sample quill 6 is placed inside the pipe 3 to obtain side stream, that is representative of the gas/liquid composition of the gas stream in pipe 3. Side stream flows through a mixing unit 8, where droplets of liquid are converted into substantially uniform-sized droplets to enable these droplets to mix with the gas so that the mixture would appear to be a single phase to a Coriolis densitometer 10. A measurement of the density is made in a densitometer 10. The densitometer 10 provides measurements or a signal, which can be correlated to the density of the mixture in the gas stream in the pipe 3. The side stream then flows through a flow regulator 12 and is fed into another gas-oil separator 13 operating at a pressure lower than that of the HP separator 2. A flow regulator 12 maintains a constant flow of the side stream so that the density measurements made by the densitometer 10 are accurate. The side stream obtained by the sample quill 6 passes through a valve 7, which, in conjunction with flow regulator 12, controls and maintains a constant flow.

In one embodiment, the foam monitoring system 50 includes a wellsite display and transmitter 16. Data/signals from the densitometer 10 are passed to the display and data transmitter 16, which displays the density and/or flow rate and/or liquid content of side stream, depending on its electronic design and calculation capacity. The connection may be wired or wireless. The transmitter 16 may be programmed to transmit data to a processor located at the wellsite or at a suitable remote location, as described below with respect to FIG. 2.

Figure 2:
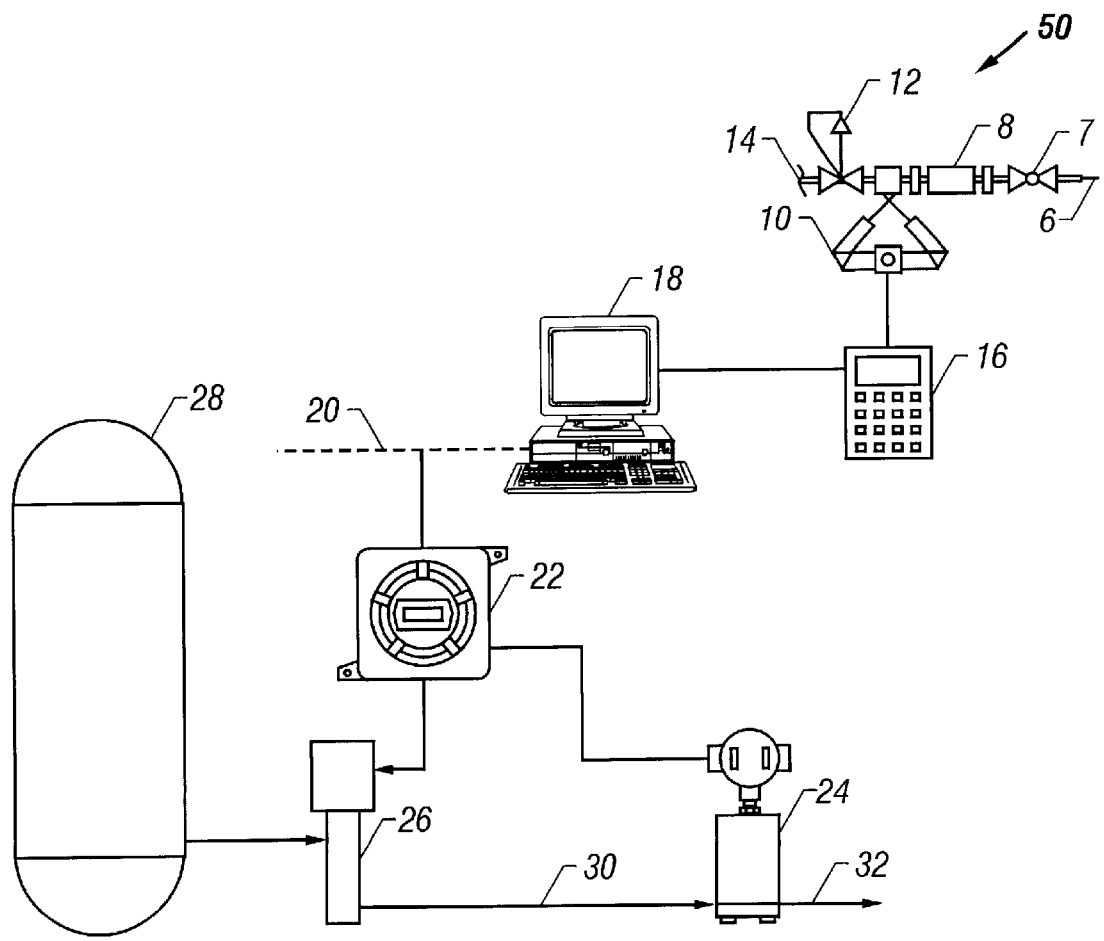
FIG. 2 is a schematic illustration of a chemical injection system for controlling chemical injection in response to foaming measurements in gas, exiting the separator shown in FIG. 1, according to one embodiment of the present invention.

FIG. 2 depicts a foam controlling aspect of the system. The local display and data transmitter 16 is connected to a control system 18, which may be a computer with the necessary computer programs and software to perform the necessary calculations, correlations, comparisons and determinations of whether foaming in separator 2 is acceptable. The control system 18 also issues the proper commands or command signals 20 to a pump controller 22 and other pump controllers (not shown) to control the injection of one or more chemicals into the formation fluid in the wellbores producing the formation fluid and/or in the separator 2 and/or in the formation fluid between the wellhead and the separator 2.

In response to the commands received from the controller system 18, the pump controller 22 adjusts the injection pump 26, which pumps an additive or additive mixture 30, from a storage tank 28 (source) through a flow meter 24 to a suitable injection location 32. The pump controller 22 polls the flow meter 24 at least periodically or, in the alternative, the flow meter 24 provides continuous feedback to the pump controller 22 with respect to the amount of the additive 30 which has actually been injected into the injection location 32. The pump controller 22 uses this information from the flow meter 24 to determine if any adjustments are needed for its commands to the injection pump 26 to change the injection rate of additive 30. Other pump controllers (not shown) control other injection pumps similar to the pump 26 shown to inject the same or different additives in a similar manner. The other pumps and the associated flow controllers are not shown in FIG. 2.

It is also within an embodiment of the present invention to use the data from the densitometer 10 as a feedback to refine the adjustment commands issued by pump controller 22 via controller system 18. A totally automated foam monitoring and controlling system may be designed in accordance with FIGS. 1 and 2. Again, the communications between various local or remote wellsite liquid content measuring devices, density measuring devices, density, flow rate and foaming display/data transmitters, control systems, computers, pump controllers, pumps and flow meters may be wired, wireless or a combination thereof. The local display/transmitter 16, and control system 18 may be integrated into a common unit. Alternatively, the display/transmitter 16 and pump controller may be combined while the control system 18 may be placed at a remote location. In that event the local unit may be programmed to determine the foam content in the gas and control the injection of the chemicals locally or via commands received from the remote control system. Thus, the present invention provides a closed-loop wellsite foam measuring and control system, wherein the system measures liquid content in a gas stream to determine the extent of foaming and in response thereto adjusts amounts of one or more chemicals/additives injected into the formation fluid or separators to control the foam level within predetermined limits. Oil from multiple wells produced at a common platform and oil from multiple wells in a common oil field is often separated by common oil/gas separator systems. In such cases, the foam monitoring and control system of the present invention may be utilized to monitor foam from each such well and control chemical injection in one or more such wells.

In one embodiment of the present invention, the foam monitoring system comprises a sample quill (or quill) equipped with a nozzle element to obtain a sample of the gas stream exiting a high pressure or HP separator and/or, if needed, other downstream liquid gas separators (intermediate (IP) or low pressure (LP) separators). The sample, which forms a slipstream or sidestream, should be a representative of the composition of the gas stream, which in most cases includes gas and liquid components. Accordingly, the quill is designed to account for various aspects of the well operation, including the flow rate of the formation fluid, the velocity (flow rate) of the gas stream, composition of the gas stream, the sizes and distributions of liquid drops or droplets in the gas stream, the pressure, temperature and other related factors. This is to eliminate or minimize any disturbance to the dynamics of the gas/liquid flows and to maintain accuracy and reproducibility of the density measurements made by a densitometer, other instrument, sensors, or methods.

The retrieval or nozzle element should be capable of obtaining or accepting the largest size of liquid droplets that could physically pass through into the gas stream exiting the HP separator or other separators if the device is placed there to monitor foaming. It is generally observed at producing wells that most liquid droplets in the gas exiting the HP separator are in the range of about 4,000 nm to about 20,000 nm in diameter. However, some studies suggest that droplets as large as 1.3 cm in diameter may exist in the gas stream. It is therefore within the embodiment of the present invention to have the nozzle element capable of accepting liquid drops or droplets up to 1.3 cm in diameter, preferably up to about 40,000 nm.

Because of the possibility of having such large-sized droplets present in the gas stream and the sidestream taken by the sample quill, it is preferred for the present invention to install a mixing unit between the sample quill and a densitometer when the latter is used to determine the density of the sidestream. The density and/or the correlated amount of the liquid in gas are then translated into the extent or degree of foaming of the gas stream either with an internal calculation mechanism incorporated into the densitometer itself or with the aid of a processor (computing device, such as a computer or a microprocessor-based processor) at the separator site or by a computing device remotely linked to the densitometer. This mixing unit is therefore connected to both the sample quill and the densitometer. Accordingly, it is downstream from the sample quill and upstream of the densitometer.

The mixing unit has the function of ensuring that any liquid drops or droplets in the sidestream are finely and uniformly dispersed in the gas phase prior to sending the sidestream to the densitometer, thus allowing the densitometer to make representative measurements and to minimize data fluctuation resulting from liquid droplet size changes. A mixing unit is needed where the densitometer cannot handle a heterogeneous sample with liquid droplets in a wide range of sizes. Also, a mixing unit may be needed to render the gas sidestream to appear to be a "single" phase gas to a particular type densitometer, such even in the presence of liquid droplets. Many densitometers may be used to provide accurate density measurements only for measuring density of such "single-phase" samples with small droplets of liquid, which cannot be obtained directly from the sidestream sample taken out of the exiting gas stream from the HP gas-oil separator.

Several different types of mixing units may be used for the present invention. For example, a static mixer with a suitable design may be used. Alternatively, a shear unit may be used. It is also within the scope of the present invention to use more than one mixing units. In such a case, the mixing units may be of the same type or different types. Several types of mixing units as commercially available and are thus not described in detail herein.

As noted above, the foaming level is determined in this invention by determining and quantifying the amount of liquid carried over by the gas exiting the HP gas-oil separator by a processor or controller at or near the separator site or at a remote location. The processor then causes a chemical injection unit to control or adjust the type and/or amount of additives injected into the separator(s) and/or the well. This provides a closed loop system, which minimizes the use of additives and chemicals for controlling foaming.

It is within the scope of the present invention to determine and to quantify the liquid either in the separators themselves or in a slip stream (also referred to as a sidestream) diverted from the gas stream exiting a gas-oil separator, particularly the HP separator, which is closest to the chokehold of the well. The measurement of liquid may be direct or indirect. A direct measurement of the amount of the liquid component in a sidestream gas by using a densitometer is preferred for the present invention. This direct measurement would allow installations of a totally automated system to monitor and control wellsite foaming. It is also within the scope of the present invention to have a remote controller or instrument to handle the information and to issue commands in response to the information to adjust the necessary treatments.

The amount of liquid in the gas may be determined by a number of methods. For instance, a batch sample can be collected over a period of time and then analyzed in a laboratory. This is an indirect method. An example of a direct method uses a suitable densitometer to measure the density of the sidestream and the density data can be correlated with the amount of liquid present in a gas stream. The amount of liquid can be correlated with foaming. It is preferred to use a densitometer to make a direct measurement of the density of the sidestream.

The measurements may be made batchwise, intermittently, semi-continuously, continuously, or in other prescribed manners familiar to those skilled in the art. It is noted here that not all of the methods may be adopted for all of the manners. For instance, if the liquid is determined by taking a sample and condensing out the droplets, it is not feasible to perform a continuous measurement. The measurement has to be batchwise or intermittently.

When a densitometer is used to make direct measurements of the density of a sidestream gas, the densitometer is placed downstream of and connected to the sample quill. If a mixing unit is used, then, as discussed earlier, the mixing unit is placed between and connected to the sample quill and the densitometer. The sidestream gas flows from the nozzle element of the sample quill, through the mixing unit to the densitometer in FIG. 1.

A preferred densitometer for making such direct measurements is a "Coriolis densitometer." A Coriolis densitometer is based on the theory of Coriolis effect. Such densitometers are commercially available and are thus not described in detail. As shown in FIGS. 1 and 2, a deflection of a flowing fluid, in a single-phase or single-phase equivalent, in a horseshoe-shaped pipe is measured. This deflection is a function of the mass flow and the density of the fluid. Accordingly, the deflection can be converted to the density of the fluid at a constant flow rate by performing calculations based on the Coriolis effect. As long as the liquid and the gas are in a single uniform phase fluid and the amount of liquid is quite small, the Coriolis densitometer can measure an equivalent density of the fluid even though this phase is not, strictly speaking, gaseous. It is therefore possible to measure the density of a gas containing a small quantity of liquid, which is finely dispersed in an annular mist regime with small droplets in the gas, the single-phase or the single-phase equivalent fluid. Gases, whether single-phase or single-phase equivalent, are not differentiated in this invention when a Coriolis densitometer is used and when the liquid droplets are smaller than 1000 nm in diameter. In this case, it is preferred to install a mixing unit between the sample quill and the densitometer.

It is preferred, as described herein, to have the droplets diameter in the range of from about 4,000 nm to about 20,000 nm to be more efficiently captured by the nozzle element of the sample quill. It is also within the present invention that two or more sensors or densitometers are used to measure either the same gas stream exiting the same separator, or different gas streams from different separators, or other combinations to provide either more measurements for more information to provide a foaming profile and/or a cross check of the accuracy/precision of the measurements.

A densitometer or other sensors used to measure the amount of liquid in the sidestream may require a downstream flow regulator in order to maintain a constant flow of the sidestream at least during the period of performing the measurement. This is particularly important when a Coriolis densitometer is used to measure the density because the Coriolis densitometer measures changes in both density and mass flow. In order to have accurate measurements of the density, the mass flow needs to be maintained as constant as practicable. Otherwise, the data obtained could be misinterpreted and the density, thus the amount of liquid, would be miscalculated. Optionally, and particularly in a continuous foam monitoring mode, it is preferred to send the sidestream gas obtained through the nozzle element of the sample quill and flowing through the densitometer to an appropriate lower pressure vessel, separator, header, storage tank or pipeline.

The liquid data, the density data and/or the resultant foaming data may be displayed on a display panel, at the wellsite or at a remote location. These data also may be sent to various controllers, controlling systems or computing devices to determine if the foaming is deteriorating, improving or remaining steady. One way of accomplishing this is by comparing the data with a predetermined limit. If foaming is outside the limit, for instance, it may be necessary to increase the amount of chemicals supplied to the formation fluid. Such controllers, controlling systems or computing devices may be at the wellsite, at a remote location, or both. Many suitable wired or wireless communicating means or their combinations may be used for receiving and sending various signals, commands, measurements, data inputs and data outputs.

The result of the foaming determination is then used as the basis of sending commands or command signals to wellsite pumps, pump controllers, or other devices, which would (1) regulate or control the rate of injecting additives into the different places such as the well itself wellbore(s), HP and other gas-oil separators, and other places of the processing equipment at the wellsite, and/or (2) provide other proper treatments including, but not limited to, varying the production rate, adjusting steam injection if there is any, adjusting the injection of chemicals for controlling corrosion etc, changing temperatures and combinations thereof. All these measures are intended to control foaming.

The term control foaming is used herein to mean defoam, antifoam, de-emulsify, or otherwise suppress foaming or inhibit foam formation. In addition to using additives or chemicals to achieve these foam controlling objectives, it is possible to use mechanical means or electromagnetic waves such as ultrasound waves or microwaves to breakup the foam, to reduce or to suppress foaming.

A number of additives are known to be effective for controlling foaming for the purposes of the present invention. For instance, U.S. Pat. No. 5,853,617, issued to the same Assignee of the present invention, discloses a method and a composition for suppressing oil-based foams by using a combination of two conventional defoamers—a fluorosilicone and a non-fluorinated siloxane.

Other suitable additive examples include conventional additives such as polydiorganosiloxanes, also known generically and generally as silicones. Polydialkylsiloxanes are preferred polydiorganosiloxanes. In particular, polydimethylsiloxanes (PDMS) are more preferred for the present invention to control foaming. Fluorosilicones, partially fluorinated silicones, PDMS-polybutadiene block copolymers, silicone-glycol compounds, silicone-silica adducts, fatty acids, hydrolyzed lipids, combinations thereof and/or with PDMS or other polydiorganosiloxanes are other examples of additives suitable for the present invention. See U.S. Pat. No. 5,853,617. To the extent that U.S. Pat. No. 5,853,617 discloses various antifoaming, defoaming, or foam-controlling additive compositions, combinations, preparations, commercial sources, uses of these additives and the method of using these additives, the patent is incorporated herein by reference.

These foaming-control additives may be used in a number of physical and/or chemical forms, such as pure (or undiluted) materials, solutions, emulsions, suspensions, blends, other type physical mixtures or admixtures, and combinations thereof. These additives may be pumped into the oil well premixed or separately, with or without any additional diluents or solvents. The same supply line or different supply lines may be used for different additives, depending on chemical and physical compatibilities, relative quantities required and other properties.

There are a number of ways the control of injections of additives may be accomplished. Depending on the number of wells at a particular site or offshore platform, the location of the controllers, the location of the operators and the degree of automation, there could be a plurality of controllers, both local and remote, a plurality of sample quills, a plurality of liquid measuring devices and a plurality of pumps, pump controllers, flow meters etc. The measurement signals, data, calculated results such as correlations and comparisons, command signals and feedback information or signals could be transmitted or communicated by wired or wireless means. Many functions can also be built into one unit, if preferred, to accord various benefits such as reducing the total number of controlling devices or units and increasing the speed of communications.

Figure 3:
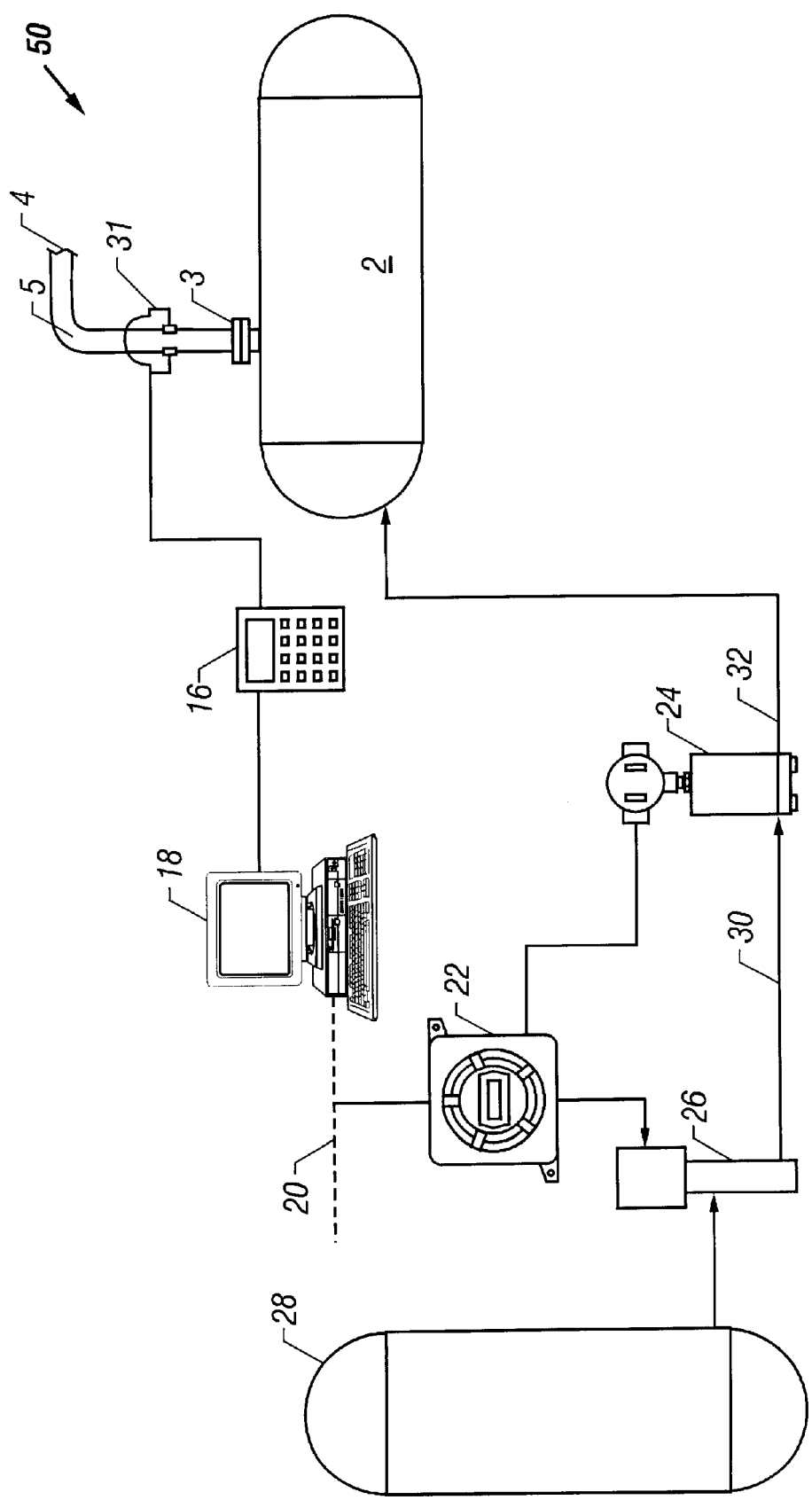
FIG. 3 illustrates a foam or carry over monitoring system according to another embodiment of the present invention, wherein a transmission probe is used to measure the density of a gas stream exiting an HP oil-gas separator.

Another preferred embodiment of the present invention includes a transmission probe device using the principle of light scatter to determine when particles of oil are present in the gas stream. As more particles pass between the source and detector, the instrument reading increases, indicating an increase in optical density and indicating an increase in the foaming activity and amount of oil carry over. FIG. 3 illustrates a foam or carry over monitoring system wherein a transmission probe is used to measure the density of a gas stream exiting an HP oil-gas separator.

In FIG. 3, a system substantially similar to that of FIG. 2 is illustrated except that instead using a densitometer to measure foaming in a side stream, a transmission probe 31 is used to measure foaming directly on the pipe 3 carrying vaporous gas 5. The transmission probe 31 shown is of a type using two elements installed on opposing sides of the pipe. In another embodiment, the transmission probe is of a type using only a single element.

Any sensor which can directly measure foaming in the vaporous gas 5 can be used with the present invention, but preferably it is of a type that uses the principle of light scatter to determine when particles of oil are present in the gas stream as function of optical density. In a preferred embodiment, the transmission probe, in addition to sending a single to the controller 18 indicating foaming could also send a signal indicating fault conditions such as power or lamp failures. When a two-element probe is used, preferable the two elements are installed on opposing sides of the pipe 3, in effect turning the pipe into a flow cell. When a single element probe is used, it may be necessary to use a side stream configuration as shown in FIGS. 1 and 2.

While the foregoing disclosure is directed to a number of the preferred embodiments of the invention, various modifications will be apparent to and appreciated by those skilled in the art. Similarly, the theories and the examples are presented solely to illustrate details of the invention so one skilled in the art would more readily understand and appreciate the advantages. It is intended that all variations within the scope and spirit of the claims be embraced by the foregoing disclosure.

What is claimed is:

1. A system for determining and optionally controlling foaming of formation fluid passing through at least one liquid and gas separator that provides a gas stream separated from the formation fluid, comprising:

a sensor for providing sensor measurements of a parameter of interest relating to a gas stream separated from a formation fluid that is indicative of foaming of the formation fluid; and a processor utilizing the sensor measurements for determining a degree of foaming of the formation fluid.

2. The system of claim 1 further comprising a gas separation device for separating a portion of gas from the gas stream to form a side stream and wherein the sensor measurements are made utilizing the side stream.

3. The system of claim 2, wherein the gas separation device is a quill.

4. The system of claim 1, wherein the sensor is a densitometer providing measurements corresponding to the density of fluid in the stream of gas.

5. The system of claim 1, wherein the sensor is a transmission probe providing measurements corresponding to the optical density of the stream of gas.

6. The system of claim 2 further comprising a mixing device for mixing fluid in the side stream and providing the mixed fluid to the sensor.

7. The system of claim 2 further comprising a regulator for regulating flow of fluid through the side stream.

8. The system of claim 7, wherein the regulator maintains a constant flow of the sidestream.

9. The system of claim 1, wherein the sensor is a transmission probe.

10. The system of claim 1, wherein the at least one separator is a high pressure vessel receiving fluid from a wellhead for separating gas from liquid, the separator further having an exit conduit for providing the gas stream.

11. The system of claim 10, wherein the sensor is mounted on the exit conduit.

12. The system of claim 1, wherein the processor displays the degree of foaming on an onsite display.

13. The system of claim 1 further comprising a chemical injection unit for supplying a chemical to the formation fluid for optionally controlling foaming of the formation fluid.

14. The system of claim 13, the chemical injection unit comprising:

a source of at least one chemical for injection into the formation fluid at a selected location thereof for at least inhibiting foam formation of foam in the formation fluid; and a chemical supply device for supplying the chemical to the selected location.

15. The system of claim 13, wherein the processor controls the operation of the chemical injection unit to increase the amount of chemical supplied to the formation fluid when the degree of foaming is outside a predefined limit.

16. The system of claim 1, wherein the processor is located at one of (i) a site of the at least one separator; and (ii) a remote location.

17. The system of claim 13, wherein the chemical injection unit injects the at least one chemical at a location selected from a group consisting of (i) in the at least one separator; (ii) in a well producing the formation fluid; (iii) at a wellhead at the surface; and (iv) in a selected number of wells from a plurality of wells providing formation fluid to the at least one separator.

* * * * *